United States Patent [19]

Issautier

[11] Patent Number: 4,684,460
[45] Date of Patent: Aug. 4, 1987

[54] HAEMODIALYSIS DEVICE AUTOMATICALLY MONITORING LOSS OF WEIGHT

[76] Inventor: Gérald Issautier, Domaine des Alpilles - Immeuble le Saint Rémy 397, Corniche Kennedy, 13007 - Marseille, France

[21] Appl. No.: 805,436

[22] Filed: Dec. 5, 1985

[30] Foreign Application Priority Data

Dec. 14, 1984 [FR] France ................................ 84 19314

[51] Int. Cl.$^4$ ............................................. A61M 1/34
[52] U.S. Cl. ..................................... 210/90; 210/143; 210/257.2; 210/321.3
[58] Field of Search .......... 210/646, 647, 90, 103–105, 210/134, 136, 137, 143, 321.3, 321.4, 416.1, 257.2, 433.2

[56] References Cited

U.S. PATENT DOCUMENTS

| | | | |
|---|---|---|---|
| 3,990,973 | 11/1976 | Boag et al. | 210/321.3 |
| 4,083,777 | 4/1978 | Hutchisson | 210/646 |
| 4,162,974 | 7/1979 | Pernic | 210/321.3 |

*Primary Examiner*—Ivars Cintins
*Attorney, Agent, or Firm*—Bucknam and Archer

[57] ABSTRACT

This invention relates to a haemodialysis device comprising a dialyzer, a reservoir of dialyzate, a cartridge for regenerating the dialyzate and a positive displacement pump with one rotor which circulates the blood and the dialyzate in two separate circuits and the conduit going from the dialyzate reservoir to the dialyzer comprises a non-return valve and a pipe which is connected in by-pass downstream of said valve and which passes through a positive displacement pump with double direction of operation and which is automatically controlled by a regulation loop.

5 Claims, 3 Drawing Figures

HAEMODIALYSIS DEVICE AUTOMATICALLY MONITORING LOSS OF WEIGHT

The present invention relates to haemodialysis devices which enable loss of weight to be automatically monitored.

It will be briefly recalled that a haemodialysis device comprises a dialyzer separated into two compartments by a semi-permeable membrane, on either side of which the blood of a patient suffering from renal insufficiency and a dialysis liquid are circulated, with the result that certain toxic substances found in the blood and which should have been purified by the kidneys, pass through the membrane and are evacuated by the dialysis liquid.

Dialysis apparatus are known in which the dialysis liquid laden with impurities is rejected. Such apparatus comprise a dialysis liquid generator which is very cumbersome.

Dialysis apparatus are also known which comprise a cartridge for purifying the dialysis liquid, with the result that this liquid may be recycled. Apparatus of this second type are less cumbersome and may be installed more easily at a patient's home.

The present invention relates to apparatus of this second type which are easy to transport.

During a dialysis session, the patient loses weight equal to the quantity of impurity-laden liquid which is passed through the dialysis membrane.

As the duration of dialysis is generally determined, the total loss of weight depends on the loss of weight per unit of time, which itself depends on the permeability of the membrane, which is a design datum, and on the transmembrane pressure, i.e. on the algebraic difference between the relative pressure, which is always positive, of the blood and the relative pressure, negative or zero, of the dialysis liquid, on either side of the membrane.

At the present time, in order to adjust the transmembrane pressure, the blood pressure is generally adjusted by means of a clamp which is located in the return tube towards the patient's vein and which is tightened more or less. Such adjustment is effected manually, which exposes the blood circuit to dangerous excess pressure.

It is an object of the present invention to provide a dialysis device which comprises means for automatically obtaining a determined loss of weight per unit of time and therefore a determined total weight loss in the course of a dialysis session of given duration.

It is another object of the present invention to provide a small, portable dialysis device which may be used at home and transported by a patient when he travels.

A haemodialysis device according to the invention is of the type comprising a dialyzer equipped with a dialysis membrane, a reservoir containing the dialysis liquid, a cartridge for regenerating the dialysis liquid and means for circulating a patient's blood through said dialyzer and for circulating the dialysis liquid in closed circuit between said reservoir, said dialyzer and said regeneration cartridge.

The objects of the invention are attained by means of a device in which the dialysis liquid conduit going from said reservoir to said dialyzer comprises a non-return valve and a by-pass which is connected to said conduit downstream of said valve and which comprises a first positive displacement pump with double direction of operation.

According to a preferred embodiment, the means for circulating the blood and the dialysis liquid are constituted by a second positive displacement pump of peristaltic type, of which the rotor crushes two supple tubes, which convey the blood and the dialysis liquid respectively with constantly proportional flowrates, and the tube conveying the blood to the inlet of the dialyzer is connected to the delivery of said pump whilst the tube which takes the dialysis liquid at the outlet of the dialyzer is connected to the suction of said pump, with the result that there is always a positive difference between the pressure of the blood and the pressure of the dialysis liquid, on either side of the dialysis membrane.

One device according to the invention comprises, in known manner, a first pressure sensor which measures the pressure of the blood in the dialyzer or at the outlet thereof and a second pressure sensor which measures the pressure of the dialysis liquid in the dialyzer or at the outlet thereof.

According to a first embodiment, a device according to the invention comprises a regulation loop which comprises means for making the difference between the signals delivered by said sensors and a comparator which compares this difference with a reference value and which emits a signal proportional to the variation between this difference and the reference value which automatically acts on the direction and on the speed of rotation of said first displacement pump in order to correct the pressure of the dialysis liquid in the direction which maintains said difference constantly equal to said reference value.

According to a second embodiment, the cartridge for regenerating the dialysis liquid is placed inside the reservoir which is connected to the rest of the apparatus by supple tubes and the device comprises a weight sensor which measures the variation of the weight of said reservoir per unit of time and a regulation loop comprising a comparator which compares said measurement with a reference value and which emits a signal proportional to the variation which automatically acts on the direction and on the speed of rotation of said first pump in order to correct the pressure of the dialysis liquid in the direction which maintains the measured weight loss per unit of time constantly equal to said reference value.

The invention results in novel haemodialysis apparatus which are apparatus of reduced weight and dimensions, which may be used at home or when travelling.

The haemodialysis apparatus according to the invention enable a patient, who is using them at home or when travelling, without being supervised by qualified staff, very simply to regulate, himself, the total weight loss per dialysis session, which is a very important factor, thanks to the devices for automatically monitoring the difference in transmembrane pressure and/or the loss of weight per unit of time with which an apparatus according to the invention is equipped.

The single peristaltic pump which circulates both the blood and the dialysis liquid by means of the same rotor, makes it possible to obtain, in all circumstances, a constant ratio between the flowrate of blood and the flowrate of dialysis liquid and a positive transmembrane pressure.

The device composed of a peristalic pump connected in by-pass downstream of a non-return valve located in the tube which conveys the dialysis liquid between the storage reservoir and the dialyzer, makes it possible efficiently and automatically to monitor the pressure of the dialysis liquid in the dialyzer and therefore the transmembrane pressure which is the essential factor of the weight loss through the membrane.

An apparatus according to the invention may be equipped with a microprocessor which calculates the reference value of the loss of weight per unit of time from two data which are the total weight loss and the duration of dialysis, which calculates the effective loss of weight per unit of time from a measurement of total weight, which compares the two values and which automatically controls the direction of operation and speed of the pump placed in by-pass in order to vary the pressure of the dialysis liquid in the desired direction so that the loss of weight per unit of time measured is constantly equal to the loss of weight per unit of time calculated.

A reference value of the pressure may also be entered in the microprocessor and the microprocessor calculates the effective transmembrane pressure from the pressures of the blood and the dialysis liquid which are transmitted thereto by two pressure sensors, it compares with the reference value and it automatically controls the direction of rotation and speed of the pump placed in by-pass in order to maintain the measured transmembrane pressure constantly equal to the reference value.

The invention will be more readily understood on reading the following description with reference to the accompanying drawings, in which:

FIG. 1 schematically shows the essential elements of a haemodialysis device according to the invention.

Figure 1:
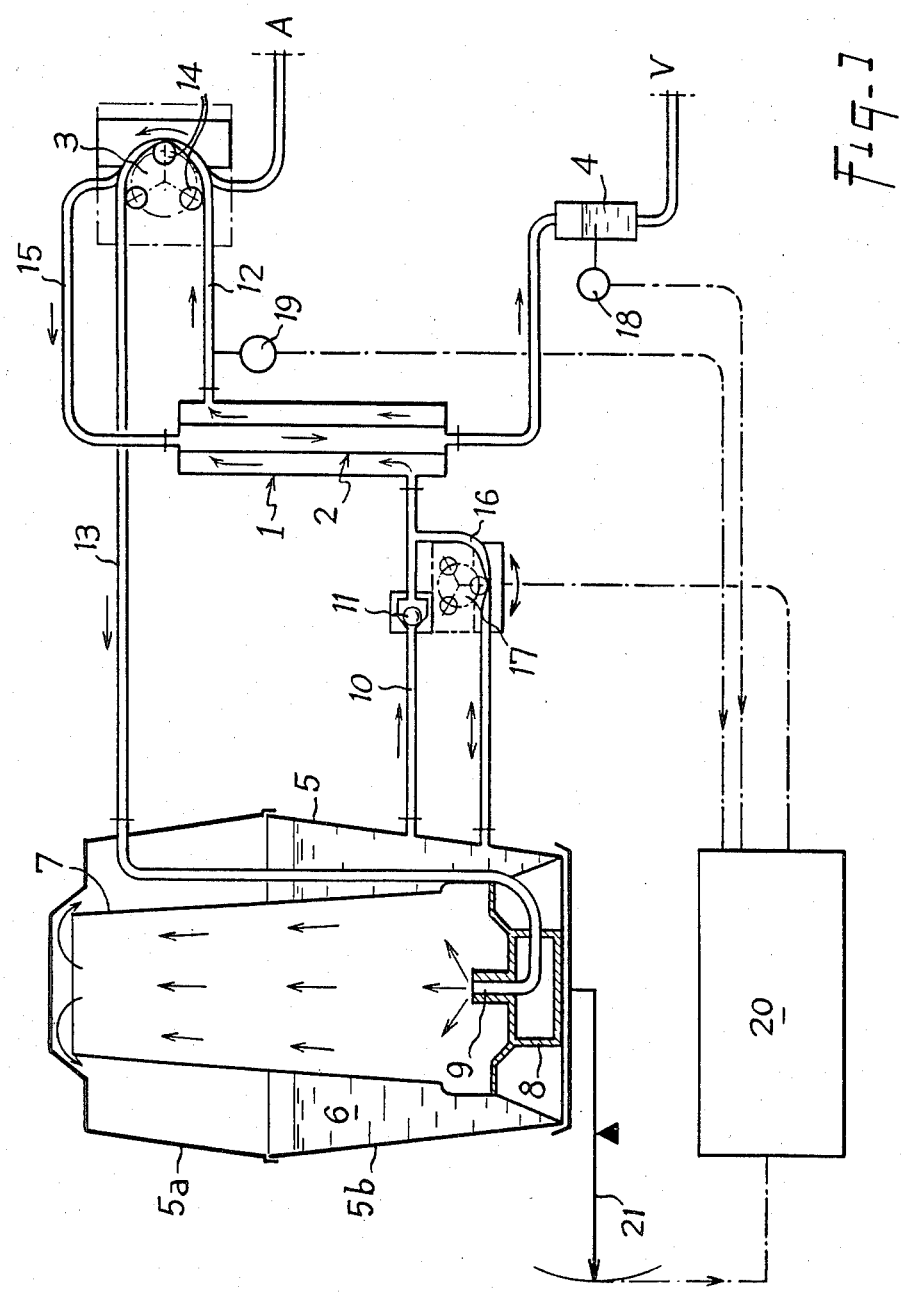

Referring now to the drawings, FIG. 1 shows a haemodialysis apparatus, also called an artificial kidney, which comprises, in known manner, a dialyzer 1, of any known type, which comprises a dialysis membrane 2, of any known type. The blood taken from an artery A of a patient is sucked by a positive displacement pump 3 which delivers it in the dialyzer 1 where it circulates in contact with one face of membrane 2. The purified blood then passes through a bubble trap 4 and it is reinjected into a vein V of the patient.

A dialysis liquid or dialyzate circulates in the dialyzer 1 in contact with the other face of the membrane 2.

A liquid laden with part of the impurities found in the blood and which should have been purified by the kidneys, in particular urea and creatinine, passes through the membrane and mixes with the dialysis liquid.

The apparatus according to FIG. 1 is designed to be a light, portable apparatus which a patient may use at home and take along whilst travelling.

It comprises a reservoir or container 5 which contains the dialysis liquid and which has a capacity of the order of 10 litres. The reservoir 5 is preferably made of plastics material, such as polyethylene, which is composed of two parts 5a, 5b interfitting or hermetically welded to each other. A cartridge 7 for regenerating the dialyzate, of any known type, is disposed vertically at the centre of reservoir 5, on a base 8 which is part of the reservoir and which comprises an axial conduit 9 which opens out at the centre of the base of the cartridge 7.

The temperature of the dialysis liquid is maintained between 37° C. and 38° C. by thermostatically controlled heating jackets placed around the container under an insulating cover.

The dialyzate 6 is taken from the bottom of the reservoir 5 by a suction pipe 10 which is provided with a non-return valve 11. The dialyzate passes through the dialyzer in which it circulates in contra-flow with respect to the blood. It leaves the dialyzer via a pipe 12 which is a supple tube which passes through the positive displacement pump 3. Pump 3 delivers the dialyzate into a supple tube 13 which penetrates in the reservoir 5 and which is connected to channel 9. It is therefore seen that the dialyzate is permanently recycled. The impurity-laden dialyzate which leaves the dialyzer 1 penetrates in the base of the regeneration cartridge 7 and passes therethrough in upward direction, whilst being purified. It leaves, purified, via the upper end of the cartridge and it falls down as a shower into the bottom of the reservoir 5.

Reservoir 5 and filtering cartridge 7 advantageously form a unit which is disposable after a session of haemodialysis.

The haemodialysis apparatus comprises certain known measuring and alarm devices. For example the bubble trap 4 is equipped with means for avoiding the risks of haemorrhage or of embolism.

It comprises, in known manner, an ultrasound emitter-receiver placed on either side of the bottom of the bubble trap 4. If the bubble trap is filled with air which would risk being taken along into vein V and provoking an embolism, the ultra-sounds are no longer transmitted and the ultra-sound detector triggers off an alarm and automatically stops the pump 3.

The bubble trap 4 is also equipped with a haemoglobin colorimetric detector which comprises a monochromatic photo-electric receiver tuned to the colour red of the haemoglobin of blood.

This detector triggers off an alarm and automatic stop if the colour red lightens or disappears, this corresponding to a drop in the level of blood in the bubble trap.

At the end of dialysis, a sachet of isotonic solution is connected to the blood circuit to rinse it. When the solution arrives in the bubble trap, the colorimetric detector automatically stops the pump 3.

The dialyzate circuit also comprises a haemoglobin colorimetric detector which detects the presence of blood in the dialyzate in the event of the membrane 2 tearing and which triggers off an alarm and automatically stops the pump 3.

All these circulation monitoring apparatus are known and have not been shown in the drawing.

The known haemodialysis apparatus comprise two distinct positive displacement pumps, one for circulating the blood and the other for circulating the dialysis liquid. This solution leads to heavy, cumbersome apparatus.

An apparatus according to the invention comprises one single positive displacement pump 3, of peristaltic type, i.e. a pump comprising a rotor which is eccentric with respect to a circular cradle and on which are mounted rollers 14 which crush supple tubes, which pass between the rollers and the cradle. The blood and the dialysis liquid circulate in two different supple tubes of different inner diameter, which are crushed by a single pump rotor, with the result that the ratio between the flowrates of blood and of dialysis liquid remains constant, whatever the speed of the pump 3.

That compartment of the dialyzer in which the blood circulates is connected to a delivery conduit 15 of pump 3, whereas that compartment of the dialyzer in which the dialyzate circulates is connected to a suction conduit 12 of pump 3. A positive difference thus exists between the relative pressure of the blood and the relative pressure of the dialyzate, on either side of the membrane 2.

One of the essential parameters of a dialysis is the volume of ultra-filtrate (water+salts) which passes through the membrane per unit of time and which determines the loss of weight of a patient for a determined duration of dialysis.

According to an essential feature, a dialysis apparatus according to the invention comprises means for automatically varying the pressure of the dialysis liquid in the dialyzer in order to vary the difference in pressure between the blood and the dialysis liquid, on either side of the membrane 2, in order to obtain a loss of weight per determined unit of time.

A pipe 16 is connected in by-pass on the suction pipe 10, between the non-return valve 11 and the dialyzer 1. This pipe, which is a supple tube, passes in a peristaltic pump 17 and it returns to the reservoir 5 in the bottom thereof.

In a variant embodiment, the pipe 16 leaving the pump 17 may be reconnected on conduit 10 upstream of valve 11. Pump 17 may be driven in one direction or in the other.

The apparatus comprises a first pressure sensor 18 which measures the relative pressure of the blood at the level of the dialyzer or at the outlet thereof, for example in the bubble trap 4. It comprises a second pressure sensor 19 which measures the relative pressure of the dialyzate at the level of the dialyzer or at the outlet thereof. The signal delivered by the sensors 18 and 19 are transmitted to a regulation device 20 which comprises a regulation loop which automatically controls the direction and speed of rotation of the pump 17.

A determined dialysis membrane has a permeability given by the designer which corresponds to the volume of liquid which passes through the membrane per unit of difference in transmembrane pressure and per unit of time. This permeability generally varies between 0.03 and 0.06 ml/Pa/hour.

In order to obtain a loss of weight per determined unit of time, a first means according to the invention consists in calculating, from the permeability of the membrane, the transmembrane pressure necessary for obtaining this loss of weight.

Regulator 20 comprises means for introducing the value calculated as reference pressure into the regulation loop. From there, the regulator 20 calculates at any instant the algebraic difference between the relative pressures measured by the sensors 18 and 19 and compares it with this reference value and it automatically varies the pressure of the dialyzate in the dialyzer by varying the direction and speed of rotation of pump 17 in order to maintain the difference in pressure equal to the reference value.

If the pressure difference measured becomes less than the reference value, the relative pressure of the dialyzate must be reduced. In that case, the regulator 20 controls start-up of pump 17, in clockwise direction, with the result that pump 17 takes part of the dialyzate having passed through the non-return valve and returns it towards reservoir 5, this reducing the pressure of the dialyzate in the dialyzer 1 and therefore increasing the difference in transmembrane pressure. If the difference in pressure remains less than the reference value, the regulator 20 increases the speed of rotation of pump 17 until the variation between the pressure difference measured by sensors 18 and 19 and the reference value is cancelled out and then maintains the speed of pump 17 constant.

If, on the contrary, the pressure difference measured is greater than the reference value, the relative pressure of the dialyzate must be increased. In that case, the regulator 20 controls the start-up of pump 17 in anticlockwise direction and increases the speed until the variation is cancelled out.

FIG. 1 shows an apparatus which comprises a weight sensor 21 which measures the variation in weight of the reservoir 5 per unit of time. Such variation in weight corresponds to the variation in weight of liquid and salts contained in reservoir 5, i.e. to the loss of weight per unit of time of the patient.

The signal emitted by sensor 21 is transmitted to regulator 20 which comprises a second regulation loop which compares the measured variation in weight with a reference value and which automatically acts on the direction and on the speed of rotation of pump 17 to vary the pressure of the dialyzate in the dialyzer, in order to return to zero the difference between the measured variation in weight and the reference value.

FIG. 1 shows an embodiment of a weight sensor in which the container 5 is mounted on the tray of electronic scales which emit an electrical signal proportional to the total weight of the container. In that case, the regulator 20 comprises a differentiator circuit which emits a signal proportional to the variation in weight per unit of time or a calculating unit which calculates such variation.

Regulator 20 may be constituted by analog regulation loops or by a microprocessor which receives the signals emitted by sensors 18, 19 and 21, which processes them and which emits a signal for controlling pump 17.

FIG. 1 shows a preferred embodiment of an apparatus which comprises a double regulation of the pressure of the dialyzate in the dialyzer, either from the difference in the pressure measured by the sensors 18 and 19, or from the measurement of the variation in weight of the container measured by sensor 21. In that case, the apparatus is equipped with a switch which makes it possible to choose one or the other of the two regulations.

In a variant embodiment, an apparatus according to the invention may comprise one of the two regulations only.

FIG. 1 shows an embodiment comprising two pressure sensors 18 and 19. In a variant embodiment, the two pressure sensors 18 and 19 may be replaced by one differential pressure sensor which directly measures the difference in transmembrane pressure.

Figure 2:
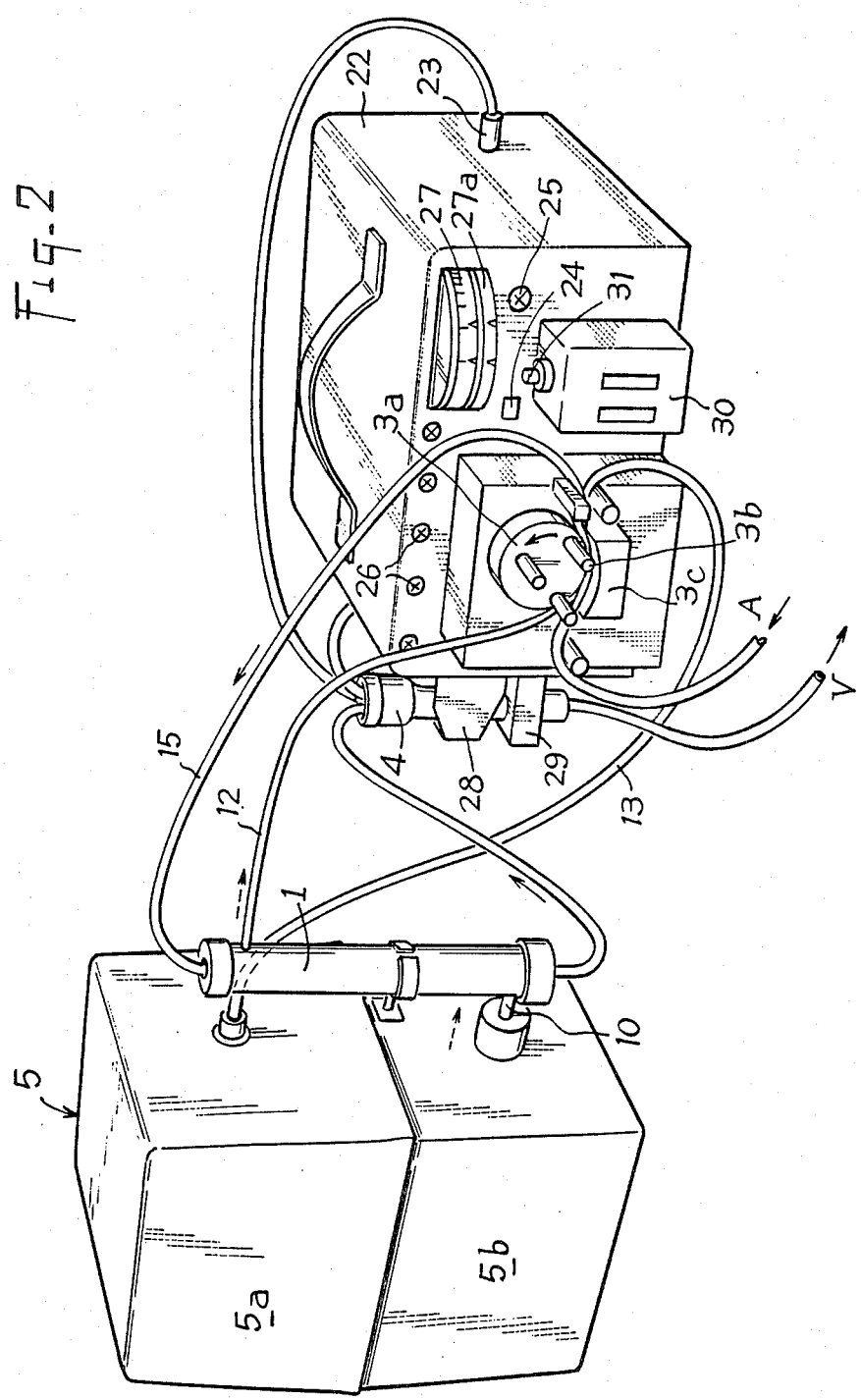
FIG. 2 is an overall view in perspective of a portable dialysis apparatus according to the invention.

FIG. 2 shows an overall view in perspective of a portable haemodialysis apparatus according to the invention.

This apparatus comprises, on the one hand, a reservoir 5 containing a regeneration cartridge which constitutes a disposable unit. It comprises a dialyzer 1 which is likewise disposable after use. It comprises a portable case 22 which contains the circulation-assisting and measuring apparatus. These components are connected together by supple tubes in which the blood and the dialysis liquid circulate.

FIG. 2 shows a perspective view of an embodiment of a portable case 22.

This case contains the positive displacement pump 3 of which is shown the rotor 3a bearing three rollers 3b. Also shown are the two supple tubes 13 and 15 in which the dialysis liquid and the blood respectively circulate, which are crushed between the rollers 3b and the circular cradle 3c of the pump.

The case 22 comprises connectors 23 of which only one is visible in the drawing, which is the one on which a supple tube for taking blood pressure is connected.

Case 22 bears on its front face a stop-start press-button 24 and a lamp 25 indicating that the apparatus is operating. It also bears five alarm lamps 26 which indicate respectively a leakage of blood in the dialyzate, a detection of air in the bubble trap, a detection of change of colour of the liquid in the bubble trap, an abnormal variation in the blood pressure and an abnormal variation in the transmembrane pressure.

Reference 27 denotes a galvanometer which displays the measurement of the blood pressure and which comprises two indexes, one of maximum pressure and the other of minimum pressure.

Reference 27a represents a second galvanometer which displays the transmembrane pressure.

The case 22 bears on one of its side faces an ultrasound probe 28 and a haemoglobin colorimetric detector 29 in the form of clamps, disposed one above the other. A transparent bubble trap 4 is engaged in the clamp formed by probe 28 and the colorimetric detector 29 which perform the function of support for the bubble trap.

Reference 30 denotes a manual/automatic switch which serves to switch on or off the automatic regulation of loss of weight.

Reference 31 denotes a push button which serves to eliminate the alarm as long as it is held by the patient.

Case 22 further contains the second peristaltic pump 17 (not visible in the drawing) as well as the circuits and electronic components of regulator 20 and the pressure sensors.

Figure 3:
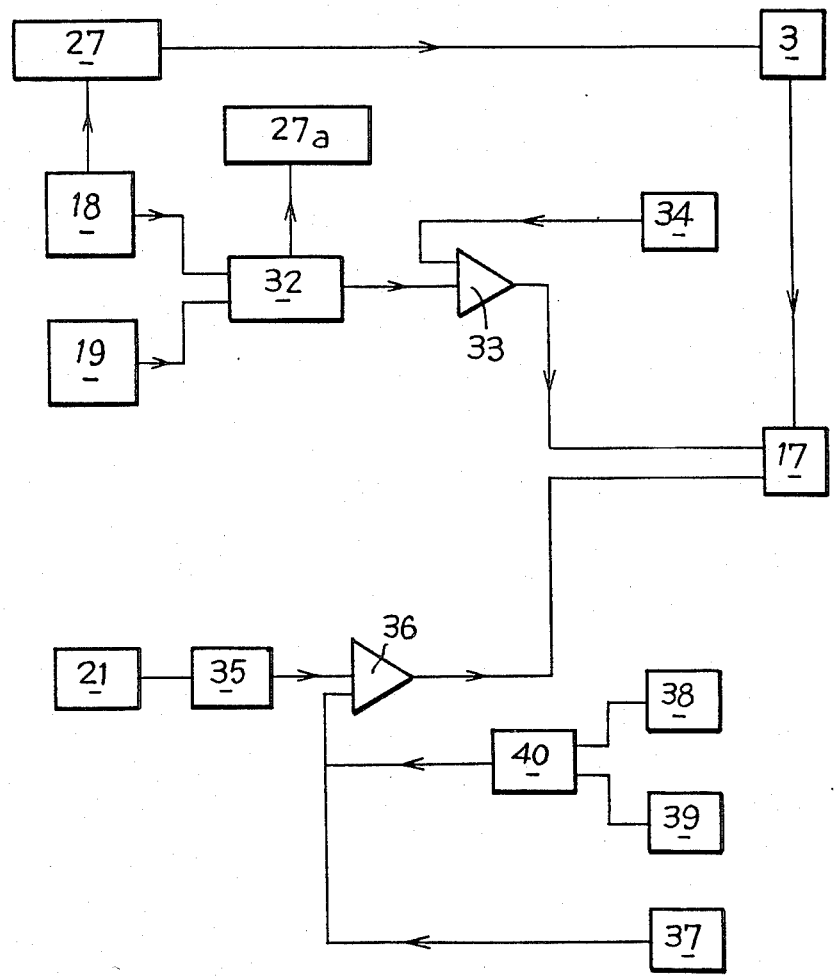
FIG. 3 is a diagram of the electronic circuits for regulating the loss of weight of the patient.

FIG.3 is a diagram of an embodiment of the electronic circuits for regulating the loss of weight per unit of time.

References 3 and 17 denote the contactors of the motors of the two peristaltic pumps.

References 18 and 19 respectively denote the blood pressure sensor and the dialyzate pressure sensor. Reference 27 is the galvanometer with contacts shown in FIG. 2 which displays the blood pressure. If the latter attains one of the thresholds fixed by the two contacts, the pump 3 is automatically stopped.

Reference 32 represents a circuit which makes the algebraic diffence between the signals delivered by sensors 18 and 19, this difference corresponding to the transmembrane pressure.

Reference 27a represents a galvanometer or a digital voltmeter which displays the transmembrane pressure. Reference 33 represents a comparator which compares the measured transmembrane pressure with a reference value which is entered manually by the patient into an input register 34 which may for example be a potentiometer in the case of an analog installation or a keyboard in the case of an installation comprising a microprocessor. The comparator 3 delivers a signal of which the polarity corresponds to the direction of variation between the calculated transmembrane pressure and the reference value and of which the intensity corresponds to the value of this variation. This signal automatically controls the direction of operation and the speed of the pump 17.

The upper part of the diagram which has just been described concerns the regulation of the loss of weight by means of a transmembrane pressure maintained constantly equal to a reference value calculated and introduced in the apparatus before the beginning of a dialysis.

The lower part of the diagram concerns the regulation of the loss of weight per unit of time by direct measurement of this loss of weight.

Reference 21 represents a weight sensor which measures the overall weight of the reservoir 5. Reference 35 represents a differentiator circuit which emits a signal proportional to the variation in weight per unit of time. Reference 36 represents a comparator which compares the measured variation in weight with a reference value.

The desired variation in weight per unit of time may be calculated by the patient and introduced manually into an input register 37.

In a variant embodiment, in the event of the apparatus comprising a calculating unit, the total weight loss to be attained during a session of dialysis may be introduced into a register 38 and the duration of dialysis into a register 39. In that case, the calculator 40 calculates the desired loss of weight per unit of time and delivers the calculated value as reference value to comparator 36.

The comparator 36 emits signal of which the polarity and intensity are proportional to the direction and to the reference value and this signal controls operation of pump 17, in the direction and at the speed which tends to cancel out this variation.

The circuits for regulating the loss of weight of the patient are circuits which comprise regulation loops which may be in the form of analog circuits or of digital means in the event of the apparatus comprising a microprocessor. The peristaltic pump 3 is controlled by the venous pressure. If the latter attains one of the two thresholds fixed by the indexes of the galvanometer 27, pump 3 stops automatically as does pump 17.

What is claimed is:

1. A haemodialysis device which comprises a dialyzer, a dialysis membrane within the dialyzer, a reservoir containing the dialysis liquid, a cartridge for regenerating the dialysis liquid located within the reservoir, means for circulating a patient's blood through said dialyzer and for circulating the dialysis liquid in closed circuit between said reservoir, said dialyzer and said regeneration cartridge, and means for automatically varying the pressure of the dialysis liquid in the dialyzer in order to vary the difference in pressure between the blood of said patient and the dialysis liquid and to control the loss of weight per unit of time, wherein the blood and dialysis liquid are circulated by a single positive displacement pump.

2. The device according to claim 1, wherein said positive displacement pump is a pump of peristaltic type having a single rotor which crushes two supple tubes, said tubes conveying the blood and the dialysis liquid respectively with constantly proportional flowrates, said dialyzer has an inlet and an outlet, the tube conveying the blood to the inlet of the dialyzer is connected to the delivery of said pump, the tube which takes the dialysis liquid to the outlet of the dialyzer is connected to the suction of said pump, whereby a positive difference is always maintained between the pressure of the blood and the pressure of the dialysis liquid, on either side of the dialysis membrane.

3. The device according to claim 1, which comprises a conduit for conveying the dialysis liquid from said reservoir to said dialyzer, wherein said means for automatically varying the pressure of the dialysis liquid in the dialyzer comprises a non-return valve placed on said conduit, a recirculation circuit by-passing said non-return valve, said circuit comprises a second positive displacement pump, a variable speed motor driving said pump in clockwise or counterclockwise direction, and means for automatically varying the direction of rotation and the speed of said pump in order to maintain a determined difference in pressure between the blood and the dialyzate in the dialyzer.

4. The device according to claim 3 which comprises a first pressure sensor which measures the pressure of the blood in the dialyzer or at the outlet thereof and a second pressure sensor which measures the pressure of the dialysis liquid in the dialyzer or at the outlet thereof, said first and second sensors delivering first and second signals, a regulation loop which comprises means for measuring the difference between said signals delivered by said sensors and a comparator which compares this difference with a reference value and which emits a third signal proportional to the variation between said measured difference and said reference value, said third signal automatically acting on the direction and on the speed of rotation of said second positive displacement pump whereby the pressure of the dialysis liquid is corrected in the direction which maintains said difference constantly equal to said reference value.

5. The device according to claim 3 wherein the cartridge for regenerating the dialysis liquid is placed inside the reservoir which is connected to said dialyzer by supple tubes and said device comprises a weight sensor which measures the variation of the weight of said reservoir per unit of time and a regulation loop comprising a comparator which compares said measurement with a reference value and which emits a signal proportional to the variation, which signal automatically acts on the direction and on the speed of rotation of said second pump in order to correct the pressure of the dialysis liquid in the direction which maintains the measured weight loss per unit of time constantly equal to said reference value.

* * * * *